United States Patent [19]  [11]  4,414,207
Nair et al.  [45]  Nov. 8, 1983

[54] RUTIN POLY(H-)SULFATE SALTS AND RELATED COMPOUNDS

[75] Inventors: Vijay G. Nair, New York; Seymour Bernstein, New City, both of N.Y.

[73] Assignee: American Cyanamid Company, Stamford, Conn.

[21] Appl. No.: 350,677

[22] Filed: Feb. 22, 1982

Related U.S. Application Data

[60] Division of Ser. No. 181,251, Aug. 25, 1980, Pat. No. 4,334,058, which is a continuation-in-part of Ser. No. 62,587, Jul. 3, 1979, abandoned, which is a continuation-in-part of Ser. No. 966,423, Dec. 4, 1978, abandoned.

[51] Int. Cl.$^3$ ............................................. A61K 31/70
[52] U.S. Cl. ........................................ 424/180; 536/8
[58] Field of Search ........................... 536/8, 118, 122; 424/180

[56]  References Cited

U.S. PATENT DOCUMENTS

| | | | |
|---|---|---|---|
| 3,953,423 | 4/1976 | Hadhanyi | 536/8 |
| 4,021,545 | 5/1977 | Nair et al. | 424/180 |
| 4,066,829 | 1/1978 | Nair et al. | 424/180 |
| 4,238,483 | 12/1980 | Frazier | 536/8 |
| 4,258,034 | 3/1981 | Joseph et al. | 536/118 |
| 4,258,180 | 3/1981 | Lewis et al. | 536/122 |

Primary Examiner—Johnnie R. Brown
Attorney, Agent, or Firm—Barbara A. Shimei; Anne M. Rosenblum

[57]  ABSTRACT

Rutin poly(H-)sulfate and salts thereof useful as complement inhibitors.

15 Claims, No Drawings

RUTIN POLY(H-)SULFATE SALTS AND RELATED COMPOUNDS

CROSS-REFERENCE TO RELATED APPLICATIONS

This application is a divisional of applicants' copending application Ser. No. 181,251, filed Aug. 25, 1980, U.S. Pat. No. 4,334,058, which is a continuation-in-part of application Ser. No. 62,587, filed July 31, 1979, now abandoned, which in turn was a continuation-in-part of application Ser. No. 966,423, filed Dec. 4, 1978, now abandoned.

BACKGROUND OF THE INVENTION

The present invention resides in the concept of novel rutin poly(H-)sulfates and salts thereof and their use as inhibitors of the complement system of warm-blooded animals.

Certain sulfated polysaccharides have been reported as having complement inhibiting activity, for example, heparin, J. Infect. Dis., 44: 250–253 (1929); carrageenin, Immunology, 8: 291 (1965); and pentosan polysulfoester, Chemical Abstracts, 75: 33179s (1971). However, no art is known which discloses anticomplementary activity for the rutin poly(H-)sulfate salts of the present invention.

A rutin sulfate sodium salt ('rutin water soluble') is commercially available from E. Merck, Darmstadt, West Germany, Catalogue No. 500014. This material, which is useful as an injectable form of Vitamin P, has an analysis, $S=5.45\%$). 'Rutin water soluble' has been tested for complement activity using the tests disclosed herein and found lacking in complement inhibiting activity. Sulfation of this material produces the rutin poly(H-)-sulfate of this invention (sulfur analysis $S=16.5\%$), which is highly active as a complement inhibiting agent.

The term "complement" refers to a complex group of proteins in body fluids that, working together with antibodies or other factors, play an important role as mediators of immune, allergic, immunochemical and/or immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935–938 (1968); Ann. Rev. Medicine, 19, 1–24 (1968); The Johns Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–66; J. Allergy Clin. Immunol., 53, 298–302 (1974); Cold Spring Harbon Conf. Cell Proliferation 2/-Proteases Biol. Control/229–241 (1975); Ann. Review of Biochemistry, 44, 697 (1975); Complement in Clinical Medicine, Disease-a-Month, (1975); Complement, Scope, December 1975; Annals of Internal Medicine, 84, 580–593 (1976); "Complement: Mechanisms and Functions", Prentice-Hall, Englewood Cliffs, N.J. (1976); Essays Med. Biochem. 2, 1–35 (1976); Hosptial Practice, 12, 33–43 (1977); Perturbation of Complement in Disease, Chap. 15 in Biological Amplification Systems in Immunology (Ed. Day and Good), Plenum, New York and London (1977); Am. J. Clin. Pathology, 68, 647–659 (1977).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389

(1969); Journal of Immunology, 119, 1–8, 1195, 1358–1364, 1482 (1977).

A variety of substances have been disclosed as inhibiting the complement system, i.e., as complement inhibitors. For example, the compounds 3,3'-ureylene-bis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327–339 (1952). German Pat. No. 2,254,893 or South African Pat. No. 727,923 discloses certain 1-(diphenylmethyl)-4-(3-phenylallyl)-piperazines useful as complement inhibitors. Other chemipal compounds having complement inhibiting activity are disclosed in, for example, Jouranl of Medicinal Chemistry, 12, 415–419; 902–905; 1049–1052; 1053–1056 (1969); Canadian Journal of Biochemistry, 47, 547–552 (1969); The Journal of Immunology, 104, 279–288 (1970); The Journal of Immunology, 106, 241–245 (1971); The Journal of Immunology, 111, 1061–1066 (1973); Biochim. Biophys. Acta, 317, 539–548 (1973); Life Sciences, 13, 351–362 (1973); Journal of Immunology, 113, 584 (1974); Immunology, 26, 819–829 (1974); Journal of Medicinal Chemistry, 17, 1160–1167 (1974); Biochim. Biophys. Res. Comm., 67, 225–263 (1975); Ann. N.Y. Acad. Sci., 256, 441–450 (1975); Journal of Medicinal Chemistry, 19, 634–639, 1079 (1976); Journal of Immunology, 118, 466 (1977); Arch. Int. Pharmacodyn.; 226, 281–285 (1977); Biochem. Pharmacol. 26, 325–329 (1977); Journal Pharm. Sci., 66, 1367–1377 (1977); Chem. Pharm. Bull., 25, 1202–1208 (1977); Biochim. Biophys. Acta, 484, 417–422 (1977) and Journal Clin. Microbiology 5, 278–284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972), 287, 452–454 (1972); Ann. Intern. Med., 84, 580–593 (1976); J. Allergy and Clin. Immunology, 60, 38–40 (1977).

Publications related to the biological use of Suramin compounds for the purpose of inhibiting the complement system, including humans, as determined by the in vivo and in vitro testing of the blood serum of warm-blooded animals are:

B. Stuber and K. Lang, Arch. Exptl, Path. Pharmacol., 154, 41–49 (1930) [C. A. 25, 3067 (1931)].

F. Klopstock, Zeitschrift für Immunitatsforschung und experimentalle Therapie, 75, 348–354 (1932).

H. J. Schmid, Schweiz. Med. Woch.- 96, 1267–1269 (1966).

K. Lauenstein, Bayer-Symposium I, 25–30 (1969).

J. S. C. Fong and R. A. Good, Clin. Exp. Immunol., 10, 127–138 (1972).

V. Eisen and C. Loveday, Br. J. Pharmac., 49, 678–687 (1973).

D. Brackertz and F. Kueppers, Allergol. Et IEt Immunopath., 11, 163–168 (1974).

E. Raepple, H-U. Hill and M. Loos, Immunochemistry, 13 (3), 251–255 (1976).

It has also been reported that the drug pentosan-polysulfoester has an anticomplementary activity on human serum, both in vitro and in vivo, as judged by the reduction in total hemolytic complement activity; Pathologie Biologie, 25, 36–-36, 25 (2), 105–108, 25 (3), 179–184 (1977).

SUMMARY OF THE INVENTION

It has now been discovered that rutin poly(H-)-sulfate salts interact with the complement reaction sequence, thereby inhibiting complement activity in body fluids.

This invention is particularly concerned with all pharmaceutically acceptable salts of rutin poly(H-)-sulfate having complement inhibiting activity of the general formula:

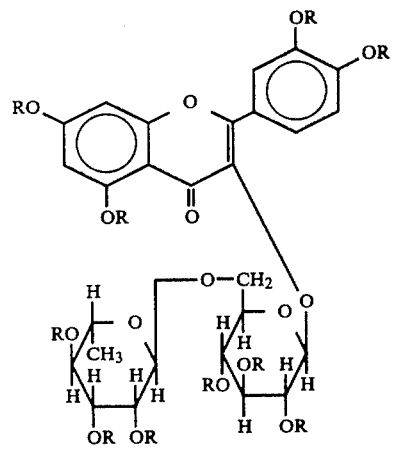

wherein each R is selected from the group consisting of hydrogen and —SO₃A; wherein A is a pharmaceutically acceptable salt cation; with the proviso that at least six of the R groups are —SO₃A.

This invention is also concerned with a method of inhibiting the complement system in a body fluid, such as blood serum, which comprises subjecting body fluid complement to the action of an effective complement inhibiting amount of rutin poly(H-)sulfate salt. The method of use aspect of this invention is further concerned with a method of inhibiting the complement system in a warm-blooded animal which comprises administering to said animal an effective complement inhibiting amount of a rutin poly(H-)sulfate salt. Body fluid can include blood, plasma, serum, synovial fluid, cerebrospinal fluid, or pathological accumulations of fluid such as pleural effusion, etc.

The rutin poly(H-)sulfate salts of the present invention fluid utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. Rutin poly(H-)-sulfate salts may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as for example, inflammation following coronary occlusion. They may also be useful in the treatment of transplant rejection and as blood culture and transport mediums.

The rutin poly(H-)sulfate salts of this invention may be prepared by the application or adaption of known methods, for example, as described in *Chemical Reviews*, 62: 549-589 (1962); and U.S. Pat. Nos. 3,271,388; 2,923,704; 2,686,779 and 2,697,093; or as described hereinbelow. It will be understood that the present sulfate salts are solvated in varying degrees with water and ethanol.

SULFATION PROCEDURE

A mixture of rutin and trialkylamine-sulfur trioxide complex in dry dimethylformamide is heated at a range from 50°-90° C. for a period of from 20-24 hours. The solution is cooled to room temperature and poured into absolute ethanol with stirring. The solvent is decanted from the separated product which is further purified with absolute ethanol. The precipitation step is repeated and purification with absolute ethanol and anhydrous diethyl ether gives the desired product which is desiccated.

EXAMPLE 1

Rutin poly(H-)sulfate, trimethylamine salt

A 3.34 g. portion of trimethylamine-sulfur trioxide complex is stirred in warm dimethylformamide to give a clear solution. A 1.22 g. portion of rutin is added and stirring is continued at 65°-70° C. for 20 hours. The solution is cooled to room temperature and poured into absolute ethanol with stirring. The pale yellow gum which separates is collected by decantation, triturated repeatedly with absolute ethanol then ether and dried in vacuo, giving the desired product as 3.5 g. of a solvated pale brown gum, (analysis: Found, S=13.1%). In another preparation, the product analysis for S=13.5%.

EXAMPLE 2

Rutin poly(H-)sulfate, sodium salt

A 3.0 g. portion of rutin poly(H-)sulfate, trimethylamine salt is dissolved in water. A 10 ml. portion of 30% aqueous sodium acetate solution is added with swirling and the mixture is allowed to stand at room temperature for 20 minutes. A 100 ml. portion of absolute ethanol is added and the resulting yellow semi-solid is separated by decantation. Trituration with absolute ethanol provides a yellow granular solid which is collected by filtration, washed with absolute ethanol, then ether and dried, giving the desired product as 1.8 g. of a solvated bright yellow powder (analysis: Found, S=15.3%) In another preparation the product analysis for S=16.8%.

EXAMPLE 3

Rutin poly(H-)sulfate, trimethylamine salt prepared from commercially available 'Rutin water-soluble'

A 3.34 g. portion of trimethylamine-sulfur trioxide complex is dissolved in 20 ml. of dimethylformamide by warming the mixture at 65°-70° C. A 1.22 g. portion of 'Rutin water-soluble' (E. Merck, Darmstadt, West Germany) is added and the mixture is stirred at 65° C. for 24 hours. The clear pale yellow solution is cooled to room temperature and 125 ml. of absolute

EXAMPLE 4

Rutin poly(H-)sulfate, sodium salt (original source commercial 'Rutin water soluble')

A 2.9 g. portion of the poly(H-)sulfate, trimethylamine salt prepared in Example 3, is dissolved in 5 ml. of water and 10 ml. of 30% aqueous sodium acetate solution is added. The mixture is filtered, allowed to stand at room temperature for 20 minutes, then 125 ml. of absolute ethanol is added with stirring. The resulting semi-solid is collected and triturated with ethanol. The resulting solid is collected by filtration, washed repeatedly with ethanol, then ether and dried in vacuo, giving 2.0 g. of the desired product as a solvated bright yellow powder (analysis: Found, S=16.5%).

EXAMPLE 5

Rutin deca (H-sulfate) Sodium Salt-"A"

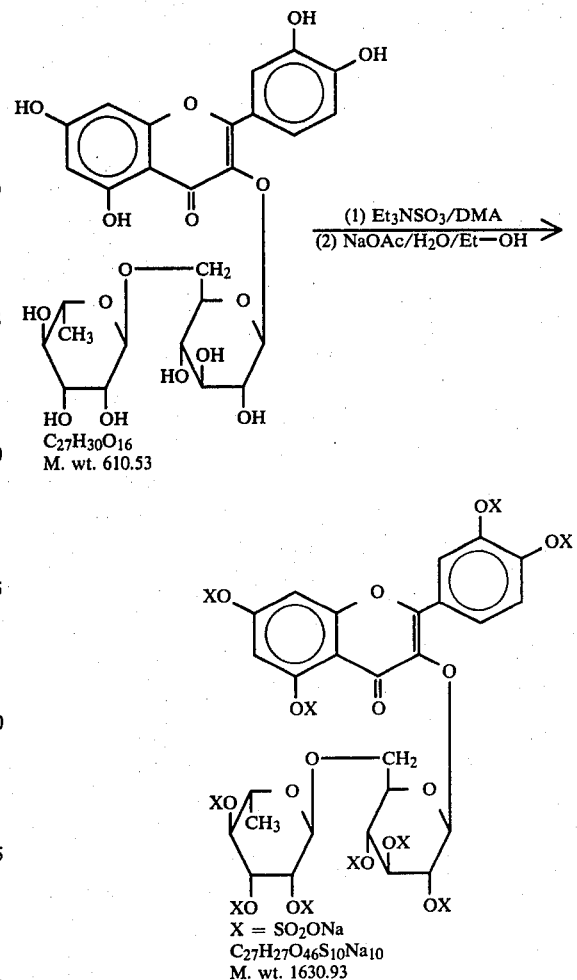

Triethylamine-sulfur trioxide (70.2 g, 0.388 mole) is dissolved in N,N-dimethylacetamide (245 ml) and Drierite (49 g) is added to it. The mixture is heated at 63°-65° for 20 minutes. Rutin (5.95 g, 9.75 mmoles) is added to the mixture with swirling and heating continued at 63°-65° for 3 hours. The reaction mixture is then rapidly cooled and filtered into acetone) (2.5 l) containing triethylamine (15 ml). The oil that separated is allowed to settle down overnight at ~0°. The supernatant liquid is decanted off and the oil washed several times with acetone to remove any excess triethylaminesulfur trioxide.

The oily product is dissolved by the addition of sodium acetate solution (30%, 40 ml) and distilled water (50 ml). The solution is allowed to stand at r.t. for 20 minutes and then filtered. The filtrate is added gradually into ethanol (2.3 l) with vigorous stirring. The stirring is continued for ~40 minutes. The granular product is filtered, washed repeatedly with ethanol and then with ether, and then dried in vacuo at r.t. for 18 hours. 14.5 g (91%) off-white powder is obtained.

Calcd for $C_{27}H_{20}O_{46}Na_{10}S_{10}$ (1630.93): C=19.88, H=1.24, S=19.66, Na=14.10. Found: C=18.98, H=2.05, S=18.25, Na=14.52, KF=2.58%.

EXAMPLE 6

Rutin nona (H-sulfate) Sodium Salt-"B"

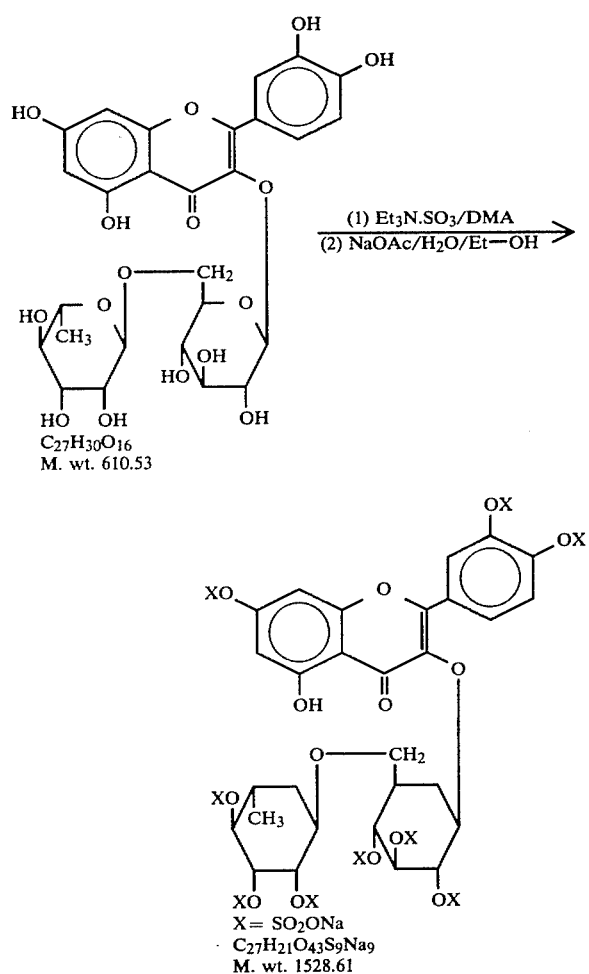

Triethylamine-sulfur trioxide (70.2 g, 0.388 mole) is dissolved in N,N-dimethylacetamide (245 ml) and Drierite (49 g) is added to it. The mixture is heated at 63°–65° for 20 minutes. Rutin (5.95 g, 9.75 mmoles) is added to the mixture with swirling and heating continued at 63°–65° for 3 hours. The reaction mixture is then rapidly cooled and filtered into acetone (2.5 l). The oil that separated is allowed to settle down overnight at r.t. The supernatant liquid is decanted off and the oil washed several times with acetone to remove any excess triethylamine-sulfur trioxide.

The oily product is dissolved by the addition of sodium acetate solution (30%, 40 ml) and distilled water (50 ml). The solution is allowed to stand at r.t. for 20 minutes and then filtered. The filtrate is added gradually into ethanol (2.3 l) with vigorous stirring. The stirring is continued for ~40 minutes. The granular product is filtered, washed repeatedly with ethanol and then with ether, and then dried in vacuo at r.t. for 18 hours. 12.8 g (86%) yellow powder is obtained.

Clcd for $C_{27}H_{21}O_{43}Na_9S_9$ (1528.61): C=21.21, H=1.38, S=18.87, Na=13.58. Found: C=19.87, H=2.61, S=17.33, Na=13.78, KF=3.37%.

EXAMPLE 7

| Preparation of Compressed Tablet | |
|---|---|
| Ingredient | mg/Tablet |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 8

| Preparation of Compressed Tablet - Sustained Action | |
|---|---|
| Ingredient | mg/Tablet |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 9

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

EXAMPLE 10

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Paraben USP | 0.02 |
| Flavoring Agent | gs |
| Purified Water qs ad | 100.0 |

EXAMPLE 11

| Preparation of Oral Liquid (Elixir) | |
|---|---|
| Ingredient | % W/V |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 12

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 13

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 14

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 15

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 16

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 17

Preparation of Dental Paste

| Ingredient | % W/W |
|---|---|
| Active Compound | 0.05–5 |
| Zinc Oxide | 15 |
| Polyethylene Glycol 4000 USP | 50 |

-continued
Preparation of Dental Paste

| Ingredient | % W/W |
|---|---|
| Distilled Water qs | 100 |

EXAMPLE 18

Preparation of Dental Ointment

| Ingredient | % W/W |
|---|---|
| Active Compound | 0.05–5 |
| Petrolatum, White USP qs | 100 |

EXAMPLE 19

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 20

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 21

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 22

Preparation of Spray Lotion (non-Aerosol)

| Ingredient | % W/W |
|---|---|
| Active Compound | 0.05–5 |
| Isopropyl Myristate | 20 |
| Alcohol (Denatured) qs | 100 |

EXAMPLE 23

| Preparation of Buccal Tablet | |
|---|---|
| Ingredient | g/Tablet |
| Active Ingredient | 0.00325 |
| 6 × Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 24

| Preparation of Lozenge | |
|---|---|
| Ingredient | g/Lozenge |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The rutin poly(H-)sulfate salts of the present invention may be administered internally, e.g., orally, or parenterally, e.g., intra-articularly, to a warm-blooded animal, to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 10 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanolamine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The rutin poly(H-)sulfate salts of the present invention may also be administered topically in the form of ointments, creams, lotions and the like, suitable for the treatment of complement dependent dermatological disorders.

Moreover, the rutin poly(H-)sulfate salts of the present invention may be administered in the form of dental pastes, ointments, buccal tablets and other compositions suitable for application periodontally for the treatment of periodontitis and related diseases of the oral cavity.

In therapeutic use, the rutin poly(H-)sulfate salts of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The sulfate salts can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the rutin poly(H-)sulfate salts of this invention has been demonstrated by one or more of the following identified tests: (i) Test Code 026 (C1 inhibitor)—This test measures the ab-lity of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesions, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported, (viii) Guinea Pig Intraperitoneal Test (GPIP)—Guinea Pigs weighing about 300 g. are dosed intraperitoneally (i.p.) with 200 mg/kg of the test compound dissolved in saline and adjusted to pH 7–8. Approximately 0.4 ml blood samples, taken by orbital sinus puncture 30 minutes and 1 hour after injections, are collected directly into centrifuge tubes; 5 ml blood samples, taken by decapitation 2 hours after injection are collected directly into diSPO® beakers. The samples were allowed to clot, centrifuged, and the resultant sera were assayed for complement activity using the capillary complement assay. Percent inhibition are calculated by comparison with simultaneous controls. The results appear in Table I together with results of Test Code 026, 035, 036, Cap 50, % inhibition and Forssman Shock. Table I shows that the principal sulfate salt of the invention possess highly significant in vitro and in vivo complement inhibiting activity in warm-blooded animals.

TABLE I

| | Biological Activities | | | | | | | |
|---|---|---|---|---|---|---|---|---|
| | In vitro activity | | | | In vivo activity (Guinea Pig) Intraperitoneal % Inhibition Time (minutes) | | | Forssman Shock |
| Compound | 026* | 035* | 036* | Cap 50* | 30 | 60 | 120 | (minutes) |
| Rutin | N | N | N | | | | | |
| Rutin Water-soluble (E. Merck) (Analysis S = 5.45%) | N | N | N | | | | | |
| Rutin poly (H—) sulfate trimethylamine salt (Analysis S = 13.1%) | +2** | N | N | >500 | | | | |
| Rutin poly (H—) sulfate sodium salt (Analysis S = 15.3%) | +7 | N | N | 69 | −79 | −89 | −89 | 17.2 (Control 3.3) |

*Code designation for tests employed as referred herein.
**Activity in wells, a serial dilution assay. Higher well number indicates higher activity. The serial dilutions are two-fold.
N = Inactive

We claim:
1. A method of inhibiting the complement system in a body fluid which comprises subjecting said body fluid to the action of an effective complement inhibiting amount of a rutin poly(H-)sulfate of the formula:

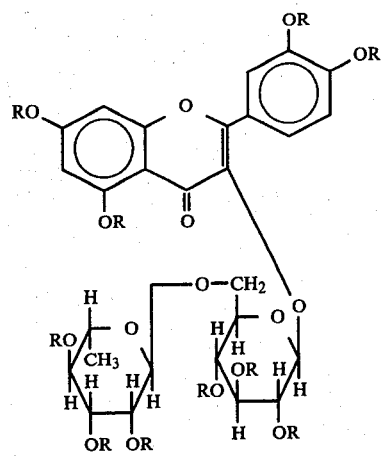

wherein each R is selected from the group consisting of hydrogen and —SO₃A; wherein A is a pharmaceutically acceptable salt cation; with the proviso that at least six of the R groups are —SO₃A.

2. A method according to claim 1, wherein the body fluid is blood serum.

3. A method according to claim 1, wherein the rutin poly(H-)sulfate is rutin poly(H-)sulfate trimethylamine salt.

4. A method according to claim 1, wherein the rutin poly(H-)sulfate is rutin poly(H-)sulfate, sodium salt.

5. A method according to claim 1, wherein the rutin poly(H-)sulfate is rutin deca(H-)sulfate sodium salt.

6. A method according to claim 1, wherein the rutin poly(H-)sulfate is rutin nona(H-sulfate)sodium salt.

7. A method of inhibiting the complement system in a warm-blooded animal which comprises administering to said animal an effective complement inhibiting amount of a rutin poly(H-)sulfate of the formula:

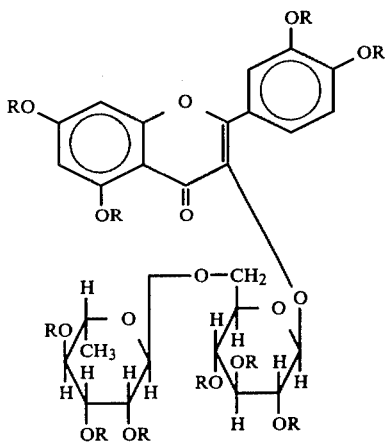

wherein each R is selected from the group consisting of hydrogen and —$SO_3A$; wherein A is a pharmaceutically acceptable salt cation; with the proviso that at least six of the R groups are —$SO_3A$.

8. A method according to claim 7, wherein the rutin poly(H-)sulfate is rutin deca(H-sulfate)sodium salt.

9. A method according to claim 7, wherein the rutin poly(H-)sulfate is rutin nona(H-sulfate)sodium salt.

10. A method according to claim 7, wherein the rutin poly(H-)sulfate is administered internally.

11. A method according to claim 7, wherein the rutin poly(H-)sulfate is administered topically.

12. A method according to claim 7, wherein the rutin poly(H-)sulfate is administered periodontally in the oral cavity.

13. A method according to claim 7, wherein the rutin poly(H-)sulfate is administered intra-articularly.

14. A method according to claim 7, wherein the rutin poly(H-)sulfate is rutin poly(H-)sulfate, trimethylamine salt.

15. A method according to claim 7, wherein the rutin poly(H-)sulfate is rutin poly(H-)sulfate, sodium salt.

* * * * *